US006939842B2

(12) United States Patent
Hunter et al.

(10) Patent No.: US 6,939,842 B2
(45) Date of Patent: Sep. 6, 2005

(54) LAUNDRY TREATMENT COMPOSITIONS COMPRISING A SILICONE AND A SUBSTITUTED POLYSACCHARIDE

(75) Inventors: Robert Alan Hunter, Bebington (GB); Christopher Clarkson Jones, Bebington (GB); Giovanni Francesco Unali, Bebington (GB)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 229 days.

(21) Appl. No.: 10/225,864

(22) Filed: Aug. 22, 2002

(65) Prior Publication Data

US 2003/0119708 A1 Jun. 26, 2003

(30) Foreign Application Priority Data

Aug. 31, 2001 (GB) .............................. 0121148
Sep. 28, 2001 (GB) .............................. 0123380

(51) Int. Cl.⁷ .............................. C11D 3/22; C11D 9/36
(52) U.S. Cl. ....................... 510/470; 510/473; 510/466; 536/123.1
(58) Field of Search ................ 510/470, 473, 510/466; 536/123.1

(56) References Cited

U.S. PATENT DOCUMENTS

| 4,518,727 A |   | 5/1985 | Traver |
| 4,973,680 A | * | 11/1990 | Billmers ...................... 536/58 |
| 5,730,760 A |   | 3/1998 | Kirk et al. |
| 6,248,710 B1 | * | 6/2001 | Bijsterbosch et al. ....... 510/470 |
| 6,288,022 B1 | * | 9/2001 | Clark et al. .................. 510/470 |
| 6,398,911 B1 | * | 6/2002 | Schroeder et al. ....... 162/164.4 |
| 6,506,220 B2 | * | 1/2003 | Clark et al. ................. 8/115.51 |
| 6,734,299 B1 | * | 5/2004 | Clark et al. .............. 536/123.1 |

FOREIGN PATENT DOCUMENTS

| GB | 1 031 484 | 6/1966 |
| JP | 05 032520 | 2/1993 |
| WO | 92/13014 | 8/1992 |
| WO | 95/35087 | 12/1995 |
| WO | 98/00500 | 1/1998 |
| WO | 98/29528 | 7/1998 |
| WO | 99/14245 | 3/1999 |
| WO | 99/14295 | 3/1999 |
| WO | 99/21892 | 5/1999 |
| WO | 99/41348 | 8/1999 |
| WO | 00/18861 | 4/2000 |

OTHER PUBLICATIONS

GB Search Report No. GB 0123380.8, dated Apr. 11, 2002, 1 p.
International Search Report No. PCT/EP 02/09228, dated Jan. 7, 2003, 4 pp.
Patent Abstracts of Japan (JP 05 032520) vol. 017, No. 327 (C–1073), dated Jun. 22, 1993—1 page.

* cited by examiner

Primary Examiner—Charles Boyer
(74) Attorney, Agent, or Firm—Alan A. Bornstein

(57) ABSTRACT

A composition comprising a silicone and a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

26 Claims, No Drawings

LAUNDRY TREATMENT COMPOSITIONS COMPRISING A SILICONE AND A SUBSTITUTED POLYSACCHARIDE

TECHNICAL FIELD

The present invention relates to compositions comprising a substituted polysaccharide of the kind comprising a benefit agent and a deposition aid for deposition of the benefit agent onto a substrate, and a silicone. These compositions are suitable, for example, for use as laundry treatment compositions or as components thereof. It further relates to a method of depositing a silicone from solution or dispersion, onto a substrate by means of such a composition.

BACKGROUND OF THE INVENTION

The deposition of a benefit agent onto a substrate, such as a fabric, is well known in the art. In laundry applications typical "benefit agents" include fabric softeners and conditioners, soil release polymers, sunscreens; and the like. Deposition of a benefit agent is used, for example, in fabric treatment processes such as fabric softening to impart desirable properties to the fabric substrate.

Conventionally, the deposition of the benefit agent has had to rely upon the attractive forces between the oppositely charged substrate and the benefit agent. Typically this requires the addition of benefit agents during the rinsing step of a treatment process so as to avoid adverse effects from other charged chemical species present in the treatment compositions. For example, cationic fabric conditioners are incompatible with anionic surfactants in laundry washing compositions.

Such adverse charge considerations can place severe limitations upon the inclusion of benefit agents in compositions where an active component thereof is of an opposite charge to that of the benefit agent. For example, cotton is negatively charged and thus requires a positively charged benefit agent in order for the benefit agent to be substantive to the cotton, i.e. to have an affinity for the cotton so as to absorb onto it.

Often the substantivity of the benefit agent is reduced and/or the deposition rate of the material is reduced because of the presence of incompatible charged species in the compositions. However, in recent times, it has been proposed to deliver a benefit agent in a form whereby it is substituted onto another chemical moiety which increases its affinity for the substrate in question.

PRIOR ART

WO-A-98/00500 discloses detergent compositions comprising a peptide or protein deposition aid having a high affinity for fibres or a surface, and a benefit agent attached/adsorbed to the deposition aid. However, this deposition aid does not change chemically such as to increase its affinity for the substrate during the treatment process.

GB-A-1 031 484 discloses stable aqueous dispersions of elastic copolymers which can be converted to cross-linked polymers by the action of heat or acid. They can be used to produce films or covering layers. However, none of the compounds has a benefit agent attached to the deposition enhancing part. There is no disclosure of using these materials in methods of laundry or fabric care.

U.S. patent application No. 5,730,760 discloses a process of fabric washing in which a dye redeposition inhibiting agent is used. The dye redeposition inhibiting polymer used is of a specific type, being produced by polymerising, for example, vinylester monomers. There is not any mention of materials having any surface substantive properties nor is there a description of any reaction by which such surface substantive properties increase during use.

WO-A-92/13114 discloses hair fixative polymers which form a film after application. The polymers are fundamentally different from those of the present invention in that they do not comprise a deposition part attached to a benefit agent. The polymeric material has no particular affinity for hair—it is just applied onto it. There is certainly no mention of a reaction which increases the affinity. Any reaction which occurs leads to the cross-linking of polymer and the formation of film. It is not disclosed that the polymers should be water-soluble of dispersible—they are normally dissolved in an inert carrier such as alcohol.

WO-A-95/35087 discloses a hair fixative amphoteric polymer composition. It is insoluble in water but can be solubilised by use of neutralisers or solubilising alcohol/water mixtures. The polymers do not to undergo any reaction which increases their affinity for hair. There is no benefit agent attached to the polymer.

WO-A-98/29528 discloses cellulose ethers in which some substituents are (poly)alkoxylated, analogues of the latter in which the (poly)alkoxylated groups are terminated with a cationic moiety in the form of a quaternary ammonium group, and cellulose ethers in which some substituents are carboxylic acids in the salt form (i.e. the materials are essentially carboxymethylcellulose variants). None of these substituents in any variant is of a kind which would undergo a chemical change to enhance fabric affinity.

WO-A-99/14245 discloses laundry detergent compositions containing cellulosic based polymers to provide appearance and integrity benefits to fabrics. These polymers are cellulosic polymers in which the saccharide rings have pendant oxygen atoms to which substituents 'R' are bonded, i.e. they are attached to the rings via an ether linkage. The groups 'R' can be hydrogen, lower alkyl or alkylene linkages terminated by carboxylic acid, ester or amide groups. Optionally, up to five alkyleneoxy groups may be interspersed between the groups are the respective oxygen atom. None of the pendant groups is a benefit agent group. However, at least some of these groups may undergo a chemical change such as hydrolysis, in the wash liquor. However no such change would result in an increased affinity for the fabric. On the contrary, because the "ester" group is configured with the carbonyl group closer to the polysaccharide than the oxygen atom (i.e. esters of carboxyalkyl groups), any hydrolysis will result in free acid substituents which will actually result in an increase in solubility and therefore, a decrease in affinity for the fabric.

WO-A-99/14295 discloses structures analogous to those described in WO-A-99/14245 but in one alternative, the substituents 'R' together with the oxygen on the saccharide ring, constitute pendant half-esters of certain dicarboxylic acids. A single example of such a material is given. Again, no pendant group is a benefit agent group. However, the dicarboxylic acid half-esters would tend to hydrolyse in the wash liquor and thereby increase affinity of the material for a cotton fabric. However, first, this mechanism of action or behaviour is not mentioned. Second, the hydrolysis rate of such dicarboxylic acids half esters is not as great as that of esters of monocarboxylic acids (which are not disclosed or claimed in WO-A-99/14295). Third, the degree of substitution for this variant is specified as being from 0.001 to 0.1.

This is so low as to make the enhancement of fabric affinity too low to be worthwhile for this mechanism of action. Fourth, the structures described and claimed insofar as they have such half ester substituents, must also have substituents of the type which are carboxyalkyl groups or esters thereof, i.e. of the type also described in WO-A-99/14245. In the latter (ester) case, these would hydrolyse to the free acid form. The degree of substitution of the latter (0.2 to 2) is considerably higher than for the half-ester groups and the resultant increase in solubility would easily negate any enhanced affinity for the fabric by hydrolysis of the half-ester groups.

WO-A-00/1 8861 provides a water-soluble or water-dispersible material for deposition onto a substrate during a treatment process, wherein the material comprises:
 (i) a deposition enhancing part having a polymeric backbone; and
 (ii) a benefit agent group attached to the deposition enhancing part by a hydrolytically stable bond;
such that the material undergoes during the treatment process, a chemical change which does not involve the hydrolytically stable bond and by which change the affinity of the material onto the substrate is increased. The preferred materials are substituted polysaccharides.

WO-A-00/18861 mentions as possible benefit groups, lubricants, ironing aids and fabric softeners. However, it is known that silicone materials are especially useful agents for delivering this kind of benefit. Our UK patent application no. 0121148.1, unpublished at the priority date of this application, describes and claims a substituted $\beta_{1-4}$ linked polysaccharide having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

We have now found that these substituted polysaccharides can be incorporated in compositions containing a silicone per se to enhance deposition of the silicone.

DEFINITION OF THE INVENTION

A first aspect of the present invention provides a composition (e.g. a chemical composition or a laundry treatment composition) comprising a silicone and a substituted polysaccharide comprising, $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

A second aspect of the present invention provides a method for depositing a silicone onto a substrate, the method comprising, contacting in an aqueous medium, the substrate and a composition according to the first aspect of the invention.

A further aspect of the invention provides the use of a composition according to the first aspect of the invention to enhance the softening benefit of a laundry treatment composition on a substrate.

DETAILED DESCRIPTION OF THE INVENTION

The Silicone

Silicones are conventionally incorporated in laundry treatment (e.g. wash or rinse) compositions to endow antifoam, fabric softening, ease of ironing, anti-crease and other benefits. Any type of silicone can be used to impart the lubricating property of the present invention however, some silicones and mixtures of silicones are more preferred.

Typical inclusion levels are from 0.01% to 25%, preferably from 0.1% to 5% of silicone by weight of the total composition.

Suitable silicones include:

non-volatile silicone fluids, such as poly(di)alkyl siloxanes, especially polydimethyl siloxanes and carboxylated or ethoxylated varients. They may be branched, partially cross-linked or preferably linear.

aminosilicones, comprising any organosilicone having amine functionality for example as disclosed in EP-A-459 821, EP-A-459 822 and WO 02/29152. They may be branched, partially cross-linked or preferably linear.

any organosilicone of formula H-SXC where SXC is any such group hereinafter defined, and derivatives thereof.

reactive silicones and phenyl silicones

The choice of molecular weight of the silicones is mainly determined by processability factors. However, the molecular weight of silicones is usually indicated by reference to the viscosity of the material. Preferably, the silicones are liquid and typically have a viscosity in the range 20 cStokes to 300,000 cStokes. Suitable silicones include dimethyl, methyl (aminoethylaminoisobutyl) siloxane, typically having a viscosity of from 100 cStokes to 200 cStokes with an average amine content of ca. 2 mol % and, for example, Rhodorsil Oil 21645, Rhodorsil Oil Extrasoft and Wacker Finish 1300.

More specifically, materials such as polyalkyl or polyaryl silicones with the following structure can be used:

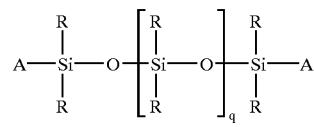

The alkyl or aryl groups substituted on the siloxane chain (R) or at the ends of the siloxane chains (A) can have any structure as long as the resulting silicones remain fluid at room temperature.

R preferably represents a phenyl, a hydroxy, an alkyl or an aryl group. The two R groups on the silicone atom can represent the same group or different groups. More preferably, the two R groups represent the same group preferably, a methyl, an ethyl, a propyl, a phenyl or a hydroxy group. "q" is preferably an integer from about 7 to about 8,000. "A" represents groups which block the ends of the silicone chains. Suitable A groups include hydrogen, methyl, methoxy, ethoxy, hydroxy, propoxy, and aryloxy.

Preferred alkylsiloxanes include polydimethyl siloxanes having a viscosity of greater than about 10,000 centistokes (cst) at 25° C.; and a most preferred silicone is a reactive silicone, i.e. where A is an OH group.

Suitable methods for preparing these silicone materials are disclosed in U.S. Pat. Nos. 2,826,551 and 3,964,500.

Other useful silicone materials include materials of the formula:

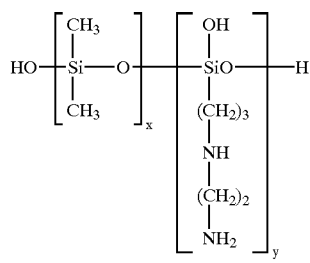

wherein x and y are integers which depend on the molecular weight of the silicone, the viscosity being from about 10,000 (cst) to about 500,000 (cst) at 25° C. This material is also known as "amodimethicone".

Other silicone materials which can be used, correspond to the formulae:

wherein G is selected from the group consisting of hydrogen, phenyl, OH, and/or $C_{1-8}$ alkyl; a denotes 0 or an integer from 1 to 3; b denotes 0 or 1; the sum of n+m is a number from 1 to about 2,000; $R^1$ is a monovalent radical of formula $C_pH_{2p}L$ in which p is an integer from 2 to 8 and L is selected from the group consisting of

—$N(R^2)CH_2$—$CH_2$—$N(R^2)_2$.

—$N(R^2)_2$;

—$N^{+}(R^2)_3 A^-$; and

—$N^+(R^2)CH_2$—$CH_2N^+H_2A^-$ wherein each $R^2$ is chosen from the group consisting of hydrogen, phenyl, benzyl, a saturated hydrocarbon radical, and each $A^-$ denotes a compatible anion, e.g. a halide ion; and

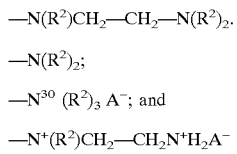

wherein $$Z = \text{—CH}_2\text{—CH(OH)—CH}_2\text{—O—(CH}_2)_3\text{—};$$

$R^3$ denotes a long chain alkyl group; and f denotes an integer of at least about 2.

Another silicone material which can be used, has the formula:

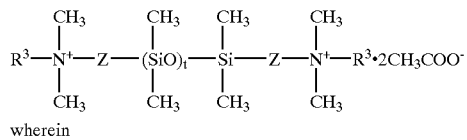

wherein n and m are the same as before.

Other suitable silicones comprise linear, cyclic, or three-dimensional polyorganosiloxanes of formula (I)

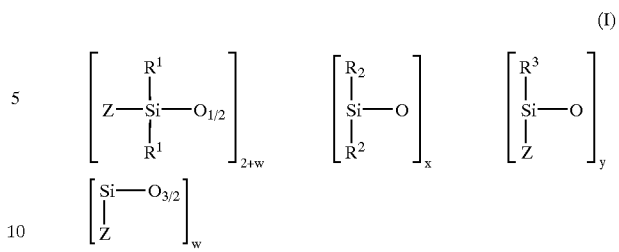

wherein
(1) the symbols Z are identical or different, represent $R^1$, and/or V;
(2) $R^1$, $R^2$ and $R^3$ are identical or different and represent a monovalent hydrocarbon radical chosen from the linear or branched alkyl radicals having 1 to 4 carbon atoms, the linear or branched alkoxy radicals having 1 to 4 carbon atoms, a phenyl radical, preferably a hydroxy radical, an ethoxy radical, a methoxy radical or a methyl radical; and
(3) the symbols V represent a group of sterically hindered piperidinyl functions chosen from

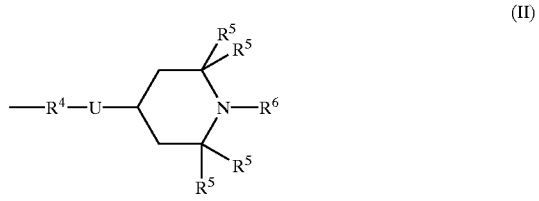

or

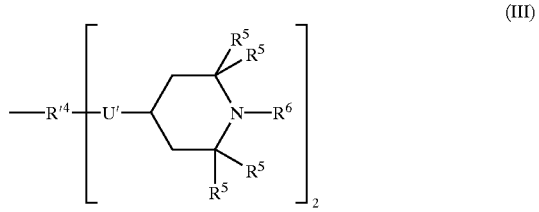

For the groups of formula II

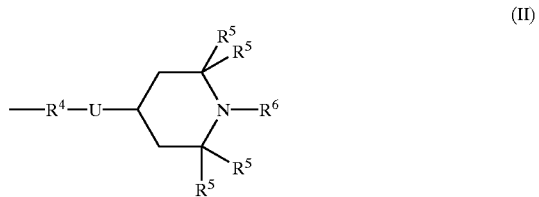

$R^4$ is a divalent hydrocarbon radical chosen from
  linear or branched alkylene radical, having 2 to 18 carbon atoms;
  linear or branched alkylene-carbonyl radical where the alkylene part is linear or branched, comprising 2 to 20 carbon atoms;
  linear or branched alkylene-cycolhexylene where the alkylene part is linear or branched, comprising 2 to 12 carbon atoms and the cyclohexylene comprises an OH group and possibly 1 or 2 alkyl radicals having 1 to 4 carbon atoms;
  the radicals of the formula —$R^7$—O—$R^7$ where the $R^7$ radical is identical or different represents an alkylene radical having 1 to 12 carbon atoms;

the radicals of the formula —R$^7$—O—R$^7$ where the R$^7$ radical is as indicated previously and one or both are substituted by one or two OH groups;

the radicals of the formula —R$^7$—COO—R$^7$ where the —R$^7$ radicals are as indicated previously;

the radicals of formula R$^8$—O—R$^9$—O—CO—R$^8$ where the R$^8$ and R$^9$ radicals are identical or different, represent alkylene radicals and have 2 to 12 carbon atoms and the radical R$^9$ is possibly substituted with a hydroxyl radical;

U represents —O— or —NR$^{10}$—, R$^{10}$ is a radical chosen from a hydrogen atom, a linear or branched alkyl radical comprising 1 to 6 carbon atoms and a divalent radical of the formula:

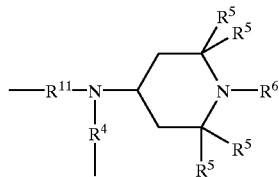

where R$^4$ is as indicated previously, R$^5$ and R$^6$ have the meaning indicated below et R$^{11}$ represents a divalent alkylene radical, linear or branched, having 1 to 12 carbon atoms, one of the valent bonds (one of R$^{11}$) is connnected to an atom of —NR$^{10}$—, the other (one of R$^4$) is connected to a silicone atom;

the radical R$^5$ is identical or different, chosen from the linear or branched alkyl radicals having 1 to 3 carbon atoms and the phenyl radical;

the radical R$^6$ represents a hydrogen radical or the R$^5$ radical or O.

For the groups of formula (III):

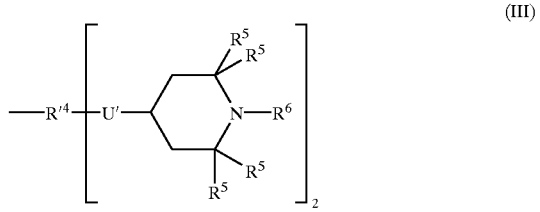
(III)

R$'^4$ is chosen from a trivalent radical of the formula:

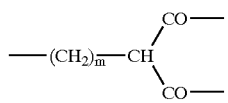

where m represents a number between 2 and 20, and a trivalent radical of the formula:

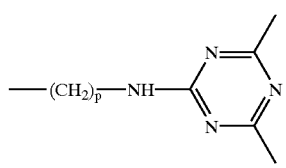

where p represents a number between 2 and 20;

U represents —O— or NR$^{12}$, R$^{12}$ is a radical chosen from a hydrogen atom, a linear or branched alkyl radical comprising 1 to 6 carbon atoms;

R$^5$ and R$^6$ have the same meaning as proposed for formula (II); and (4) the number of units ηSi without group V comprises between 10 and 450 the number of units ηSi with group V comprises between 1 and 5, $0 \leq w \leq 10$ and $8 \leq y \leq 448$.

The Substituted Polysaccharide

In the substituted polysaccharide, the silicone chain is preferably attached to the polysaccharide by a covalent stable bond. That means that the bonding of the silicone should be sufficiently stable so as not to undergo hydrolysis in the environment of the treatment process for the duration of that process. For example, in laundry cleaning applications, the substituted polysaccharide should be sufficiently stable so that the bond between the silicone and polysaccharide does not undergo hydrolysis in the wash liquor, at the wash temperature, before the silicone has been deposited onto the fabric.

Preferably, the bond between the silicone and the polysaccharide is such that the decay rate constant (kd) of the material in an aqueous solution at 0.01 wt % of the material together with 0.1 wt % of anionic surfactant at a temperature of 40° C. at a pH of 10.5 is such that $k_d < 10^{-3} s^{-1}$.

The substituted polysaccharide of the present invention is water-soluble or water-dispersible in nature and comprises a polysaccharide substituted with at least one silicone attached to the polysaccharide aid by a hydrolytically stable bond.

By water-soluble, as used herein, what is meant is that the material forms an isotropic solution on addition to water or another aqueous solution.

By water-dispersible, as used herein, what is meant is that the material forms a finely divided suspension on addition to water or another aqueous solution.

By an increase in the affinity of the substituted polysaccharide for a substrate such as a textile fabric upon a chemical change, what is meant is that at some time during the treatment process, the amount of material that has been deposited is greater when the chemical change is occurring or has occurred, compared to when the chemical change has not occurred and is not occurring, or is occurring more slowly, the comparison being made with all conditions being equal except for that change in the conditions which is necessary to affect the rate of chemical change.

Deposition onto a substrate includes deposition by adsorption, co-crystallisation, entrapment and/or adhesion.

The Polysaccharide Part

The polysaccharide is preferably $\beta_{1-4}$ linked and is a cellulose, a cellulose derivative, or another $\beta$-$_{1,4}$-linked polysaccharide having an affinity for cellulose, such as mannan and glucomannan.

Preferably, the polysaccharide has only $\beta_{1-4}$ linkages. Optionally, the polysaccharide has linkages in addition to the $\beta_{1-4}$ linkages, such as $\beta_{1-4}$ linkages. Thus, optionally some other linkages are present. Polysaccharide backbones which include some material which is not a saccharide ring are also within the ambit of the present invention (whether terminal or within the polysaccharide chain).

The polysaccharide may be straight or branched. Many naturally occurring polysaccharides have at least some degree of branching, or at any rate at least some saccharide rings are in the form of pendant side groups (which are therefore not in themselves counted in determining the degree of substitution) on a main polysaccharide backbone.

A polysaccharide comprises a plurality of saccharide rings which have pendant hydroxyl groups. In the substituted polysaccharides of the present invention, at least some of these hydroxyl groups are independently substituted by, or replaced with, one or more other substituents, at least one being a silicone chain. The "average degree of substitution" for a given class of substituent means the average number of substituents of that class per saccharide ring for the totality of polysaccharide molecules in the sample and is determined for all saccharide rings.

The Deposition Enhancing Group(s)

A deposition enhancing group is a group which undergoes a chemical change in use, and is attached to the polysaccharide agent group by means of a covalent stable bond. This chemical change results in an increase of the affinity of the material for the substrate and is referred to further below.

The chemical change which causes the increased substrate affinity is preferably caused by hydrolysis, perhydrolysis or bond-cleavage, optionally catalysed by an enzyme or another catalyst. Hydrolysis of substituent ester-linked groups is typical.

By ester linkage is meant that the hydrogen of an —OH group has been replaced by a substituent such as R'—CO—, R'SO$_2$— etc to form a carboxylic acid ester, sulphonic acid ester (as appropriate) etc together with the remnant oxygen attached to the saccharide ring. In some cases, the group R' may for example contain a heteroatom, e.g. as an —NH— group attached to the carbonyl, sulphonyl etc group, so that the linkage as a whole could be regarded as a urethane etc linkage. However, the term ester linkage is still to be construed as encompassing these structures.

The average degree of substitution of these pendant groups which undergo the chemical change is preferably from 0.1 to 3 (e.g. from 0.3 to 3), more preferably from 0.1 to 1 (e.g. from 0.3 to 1)

The Silicone Chain(s)

As used herein the term "silicone chain" means a polysiloxane or derivative thereof. In the section "Preferred Overall Structure" hereinbelow, various preferred silicone chains are recited and these are typically suitable, whether or not the substituted polysaccharide conforms to the preferred overall structure, Preferred Overall Structures Preferred substituted polysaccharides of the invention are cellulosic polymers of formula (I):

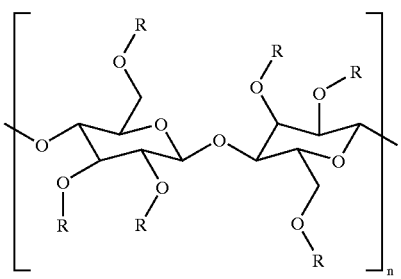

(I)

(optional ($\beta_{1-3}$ and/or other linkages and/or other groups being permitted in the above formula (I)) wherein at least one or more —OR groups of the polymer are substituted by or replaced by independently selected silicone chains and at least one or more R groups are independently selected from groups of formulae:

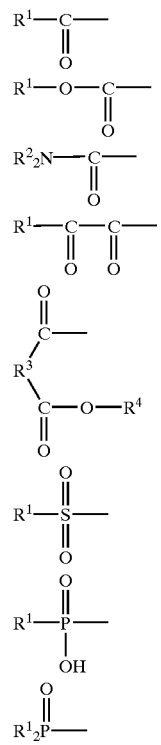

wherein each $R^1$ is independently selected from $C_{1-20}$ (preferably $C_{1-6}$) alkyl, $C_{2-20}$ (preferably $C_{2-6}$) alkenyl (e.g. vinyl) and $C_{5-7}$ aryl (e.g. phenyl) any of which is optionally substituted by one or more substituents independently selected from $C_{1-4}$ alkyl, $C_{1-12}$ (preferably $C_{1-4}$) alkoxy, hydroxyl, vinyl and phenyl groups;

each $R^2$ is independently selected from hydrogen and groups $R^1$ as hereinbefore defined;

$R^3$ is a bond or is selected from $C_{1-4}$ alkylene, $C_{2-4}$ alkenylene and $C_{5-7}$ arylene (e.g. phenylene) groups, the carbon atoms in any of these being optionally substituted by one or more substituents independently selected from $C_{1-2}$ (preferably $C_{1-4}$) alkoxy, vinyl, hydroxyl, halo and amine groups;

each $R^4$ is independently selected from hydrogen, counter cations such as alkali metal (preferably Na) or ½ Ca or ½ Mg, and groups $R^1$ as hereinbefore defined; and groups R which together with the oxygen atom forming the linkage to the respective saccharide ring forms an ester or hemi-ester group of a tricarboxylic- or higher polycarboxylic- or other complex acid such as citric acid, an amino acid, a synthetic amino acid analogue or a protein; any remaining R groups being selected from hydrogen and other substituents.

For the avoidance of doubt, as already mentioned, in formula (I), some of the R groups may optionally have one or more structures, for example as hereinbefore described. For example, one or more R groups may simply be hydrogen or an alkyl group.

Preferred groups which undergo the chemical change may for example be independently selected from one or more of acetate, propanoate, trifluroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Particularly preferred such groups are the monoacetate, hemisuccinate, and 2-(2-hydroxy-1-oxopropoxy) propanoate. The term "monoacetate" is used herein to denote those acetates with the degree of substitution of 1 or less on a cellulose or other β-1,4 polysaccharide backbone.

Cellulose esters of hydroxyacids can be obtained using the acid anhydride in acetic acid solution at 20–30° C. and in any case below 50° C. When the product has dissolved the liquid is poured into water (b.p. 316, 160). Tri-esters can be converted to secondary products as with the triacetate. Glycollic and lactic ester are most common.

Cellulose glycollate may also be obtained from cellulose chloracetate (GB-A-320 842) by treating 100 parts with 32 parts of NaOH in alcohol added in small portions.

An alternative method of preparing cellulose esters consists in the partial displacement of the acid radical in a cellulose ester by treatment with another acid of higher ionisation constant (FR-A-702 116). The ester is heated at about 100° C. with the acid which, preferably, should be a solvent for the ester. By this means cellulose acetate-oxalate, tartrate, maleate, pyruvate, salicylate and phenylglycollate have been obtained, and from cellulose tribenzoate a cellulose benzoate-pyruvate. A cellulose acetate-lactate or acetate-glycollate could be made in this way also. As an example cellulose acetate (10 g.) in dioxan (75 ml.) containing oxalic acid (10 g.) is heated at 100° C. for 2 hours under reflux.

Multiple esters are prepared by variations of this process. A simple ester of cellulose, e.g. the acetate, is dissolved in a mixture of two (or three) organic acids, each of which has an ionisation constant greater than that of acetic acid (1.82× $10^{-5}$). With solid acids suitable solvents such as propionic acid, dioxan and ethylene dichloride are used. If a mixed cellulose ester is treated with an acid this should have an ionisation constant greater than that of either of the acids already in combination.

A cellulose acetate-lactate-pyruvate is prepared from cellulose acetate, 40 per cent. acetyl (100 g.), in a bath of 125 ml. pyruvic acid and 125 ml. of 85 per cent. lactic acid by heating at 100° C. for 18 hours. The product is soluble in water and is precipitated and washed with ether-acetone. M.p. 230–250° C.

In the case of those materials having a cellulose backbone and pendant ester groups, without being bound by any particular theory or explanation, the inventors have conjectured that the mechanism of deposition is as follows.

Cellulose is substantially insoluble in water. Attachment of the ester groups to make a cellulose derivative causes disruption of the hydrogen bonding between rings of the cellulose chain or chains, thus increasing water solubility or dispersibility. In the treatment liquor, the ester groups are hydrolysed, causing the cellulose derivative to increase its affinity for the substrate, e.g. the fabric.

In the case when solubilising groups are attached to the polysaccharide, this is typically via covalent bonding and, may be pendant upon the backbone or incorporated therein. The type of solubilising group may alter according to where the group is positioned with respect to the backbone.

In this specification the "n" subscript used in the general formulae of the substituted polysaccharide is a generic reference to a polymer. Although "n" can also mean the actual (average) number of repeat units present in the polysaccharide, it is more meaningful to refer to "n" by the number average molecular weight.

The number average molecular weight ($M_n$) of the substituted polysaccharide part may typically be in the range of 1,000 to 200,000, for example 2,000 to 100,000, e.g. as measured using GPC with multiple angle laser scattering detection.

The silicone chains preferred for use to substitute or replace (dependent upon the synthetic route use to prepare the substituted polysaccharides of the invention) at least one —OR group in the compounds of formula (I) are representative of preferred silicone chains for use in substituted polysaccharides used in the invention as a whole, i.e. whether or not the overall structure conforms to formula (I).

Preferably, the average degree of substitution for the silicone chains is from 0.001 to 0.5, preferably from 0.01 to 0.5, more preferably from 0.01 to 0.1, still more preferably from 0.01 to 0.05.

Even more preferably the average degree of substitution for the silicone chains is from 0.00001 to 0.1, more preferably from 0.001 to 0,04, even more preferably from 0.001 to 0.01.

Preferred silicone chains suitable for this use are those of formula:

$$\text{—L—Si}(G^1)(G^2)(G^3)$$

wherein L is absent or is a linking group and one or two of substituents $G^1$–$G^3$ is a methyl group, the remainder being selected from groups of formula $$\text{—O}\left(\text{Si}(CH_3)_2\text{—O}\right)_n\left(\text{Si}(CH_3)(G^4)\text{—O}\right)_m\text{Si}(CH_3)_2\text{—}G^5$$

the —Si($CH_3$)$_2$O— groups and the —Si($CH_3$O)($G^4$)— groups being arranged in random or block fashion, but preferably random.

wherein n is from 5 to 1000, preferably from 10 to 200 and m is from 0 to 100, preferably from 0 to 20, for example from 1 to 20.

$G^4$ is selected from groups of formula:
—(CH$_2$)$_p$—CH$_3$, where p is from 1 to 18
—(CH$_2$)$_q$—NH—(CH$_2$)$_r$—NH$_2$ where q and r are independently from 1 to 3
—(CH$_2$)$_s$—NH$_2$, where s is from 1 to 3

$$\text{—(CH}_2)_t\text{—CH—CH}_2\text{ (epoxide)}$$

where t is from 1 to 3
—(CH$_2$)$_u$—COOH, where u is from 1 to 10, $$\text{—(CH}_2)_v\text{—(γ-butyrolactone)}$$

where v is from 1 to 10, and
—(CH$_2$ CH$_2$O)$_w$—(CH$_2$)$_x$H, where w is from 1 to 150, preferably from 10 to 20 and x is from 0 to 10;
and $G^5$ is independently selected from hydrogen, groups defined above for $G^4$, —OH, —CH$_3$ and —C(CH$_3$)$_3$.

Other Substituents

As well as the silicone chain(s) and the pendant group(s) which undergo a chemical change to enhance deposition, pendant groups of other types may optionally be present, i.e. groups which do not confer a benefit and which do not undergo a chemical change to enhance substrate affinity. Within that class of other groups is the sub-class of groups for enhancing the solubility of the material (e.g. groups which are, or contain one or more free carboxylic acid/salt and/or sulphonic acid/salt and/or sulphate groups).

Examples of solubility enhancing substituents include carboxyl, sulphonyl, hydroxyl, (poly)ethyleneoxy- and/or (poly)propyleneoxy-containing groups, as well as amine groups.

The other pendant groups preferably comprise from 0% to 65%, more preferably from 0% to 10% of the total number of pendant groups. The water-solubilising groups could comprise from 0% to 100% of those other groups but preferably from 0% to 20%, more preferably from 0% to 10%, still more preferably from 0% to 5% of the total number of other pendant groups.

Synthetic Routes

As described above, preferred substituted polysaccharides of the present invention are those of formula (I). Further, preferred silicone chains, whether for the compounds of formula (I) or any other substituted polysaccharides of the invention are preferably attached via a linking group "L". This linking group is the residue of the reactants used to form the substituted polysaccharide.

The substituted polysaccharides of the invention can be made thus:
(a) a polysaccharide is first substituted with one or more deposition enhancing groups; and
(b) one or more silicone groups are then attached.

If any other substituents are to be present, these may already be present in the commercially available polysaccharide, or attached before or after step (a) and/or (b).

Whilst steps (a) and (b) can be reversed, the reaction whereby step (a) is conducted first is preferred.

The deposition enhancing group(s) is/or are attached in step (a) according to the methodology described in WO-A-00/18861.

In step (b), one or more hydroxyl groups on the polysaccharide are reacted with a reactive group attached to the silicone chain, or the hydroxyl group(s) in question is/are converted to another group capable of reaction with a reactive group attached to the silicone chain. Listed below, are suitable mutually reactive groups. In the case of hydroxyl groups, these may be the original hydroxyl group of the polysaccharide.

However, either of a pair of these mutually reactive groups may be present on the polysaccharide and the other attached to the silicone chain, or vice versa, the reaction chemistry being chosen appropriately. In the following description, for convenience, "PSC" refers to the polysaccharide chain with or without deposition enhancing group(s) and/or other substituent(s) already attached. "SXC" refers to the group $$-\underset{\underset{G^3}{|}}{\overset{\overset{G^1}{|}}{Si}}-G^2$$

as hereinbefore defined.

Preferred linking groups -L- are selected from the following, wherein preferably, the left hand end of the group depicted is connected to the saccharide ring either direct or via the residual oxygen of one of the original saccharide —OH groups and the right hand end is connected to the moiety —Si($G^1G^2G^3$). Thus, the configuration as written is PSC-L-SXC. However, the reverse configuration SXC-L-PSC is also within the ambit of this definition and this is also mentioned where appropriate.

Preferred linking groups L are selected from amide, ester, ether, urethane, triazine, carbonate, amine and ester-alkylene linkages.

A preferred amide linkage is:

$$-G^6-\overset{\overset{O}{\|}}{C}-\underset{\underset{G^8}{|}}{N}-G^7-$$

where $G^6$ and $G^7$ are each optionally present and are independently selected spacer groups, e.g. selected from $C_{1-14}$ alkylene groups, arylene, $C_{1-4}$ alkoxylene, a residue of an oligo- or poly-ethylene oxide moiety, $C_{1-4}$ alkylamine or a polyamine groups and $G^8$ is hydrogen or $C_{1-4}$ alkyl.

This linkage can be formed by reacting $$PSC-G^6-\overset{\overset{O}{\|}}{C}-\underset{\underset{G^8}{|}}{N}-G^7-\underset{\underset{G^9}{|}}{N}H$$

wherein $G^7$ and $G^8$ are as hereinbefore defined and $G^9$ is hydrogen or $C_{1-4}$ alkyl; with a compound of formula:

$$SXC-G^6-\overset{\overset{O}{\|}}{C}-G^{11}$$

wherein $G^{11}$ is hydroxy, a group with active ester functionality halo, or a leaving group suitable for neucleophilie displacement such as imidazole or an imidazole-containing group and wherein $G^6$ is hereinbefore defined above, or —CO—$G^{11}$ is replaced by a cyclic acid anhydride. Active ester synthesis is described in M. Bodanszky, "The Peptides", Vol.1, Academic Press Inc., 1975, pp105 ff.

The reverse configuration linkage may be formed by reacting $$PSC-G^{12}-\overset{\overset{O}{\|}}{C}-G^{11}$$

wherein $G^{12}$ is a ring-opened carboxylic acid anhydride, phenylene, or a group of formula and $G^{11}$ is as hereinbefore defined;

with the group of formula

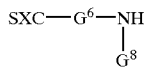

where $G^6$ and $G^8$ are as hereinbefore defined.

A preferred ester linkage has the formula

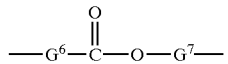

wherein $G^6$ and $G^7$ are as hereinbefore defined, $G^6$ optionally being absent.

This may be formed by reacting

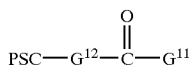

wherein $G^{11}$ and $G^{12}$ are as hereinbefore defined with

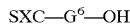

wherein $G^6$ is as hereinbefore defined.

The reverse ester linkage formation may be formed by reacting

PSC—$G^7$—OH (i.e. the optionally modified polysacharide with at least one residual —OH group) with

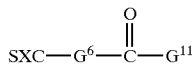

wherein $G^6$ and $G^{11}$ are as hereinbefore defined, or —CO—$G^{11}$ may be replaced by a cyclic anhydride.

Preferred ether linkages have the formula

—$G^6$—O—$G^7$— wherein $G^6$ and $G^7$ are as hereinbefore defined, optionally one being absent.

This linkage may be formed by reacting

PSC—$G^6$—OH with

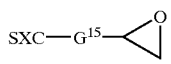

wherein $G^{15}$ is $C_{1-4}$ alkylene and $G^6$ is optionally absent and is as hereinbefore defined.

A preferred urethane linkage is

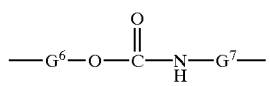

wherein $G^6$ and $G^7$ are as hereinbefore defined, $G^6$ optionally being absent (preferably absent in the configuration PSC-L-SXC)

PSC—$G^6$—OH with

SXC—$G^7$—NCO wherein $G^6$ and $G^7$ are as hereinbefore defined, $G^6$ optionally being absent (preferably absent in the configuration PSC-L-SXC)

The reverse configuration is also possible but the simplest arrangement is PSC-L-SXC and wherein $G^6$ is absent. Also most common is when $G^7$ is alkylene.

The latter compound is made by reacting

SXC—$G^7$—NH$_2$ wherein $G^7$ is as hereinbefore defined; with phosgene.

Another route is to react

PSC—$G^6$—OH wherein $G^6$ is as hereinbefore defined with carbonyl dimidazole to form

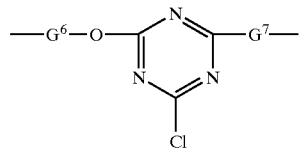

and react that product with

SXC—$G^7$—NH$_2$ wherein $G^7$ is as hereinbefore defined.

Preferred triazine linkages have the formula

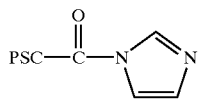

wherein $G^6$ and $G^7$ are as hereinbefore defined, $G^6$ optionally being absent.

These linkages may be formed by reacting

SXC—$G^7$—OH or

SXC—$G^7$—NH$_2$ wherein $G^7$ is as hereinbefore defined with cyanuic chloride and then with

PSC—$G^6$—OH wherein $G^6$ is as hereinbefore defined but may be absent; or (reverse -L-) by reacting

PSC—$G^7$—OH with cyanuric chloride (when $G^7$ is as hereinbefore defined) and then with

SXC—$G^6$—OH or

SXC—$G^6$—NH$_2$

Preferred carbonate linkages have the formula $$—O—\overset{\overset{O}{\|}}{C}—O—G^6—$$

wherein $G^6$ is as hereinbefore defined.
This linkage may be formed by reacting

PSC—OH with

SXC—$G^6$—OH in the presence of carbonyl dimidazole or phosgene
Preferred amine linkages have the formula $$—G^6—\overset{\overset{O}{\|}}{C}—\underset{\underset{G^8}{|}}{N}—G^7—\underset{\underset{G^9}{|}}{N}\diagdown\underset{OH}{\diagdown}G^{15}—$$

wherein $G^6$, $G^7$, $G^8$, $G^9$ and $G^{15}$ are as hereinbefore defined.
This linkage may be formed by reacting $$PSC—G^6—\overset{\overset{O}{\|}}{C}—\underset{\underset{G^8}{|}}{N}—G^7—\underset{\underset{G^9}{|}}{NH}$$

wherein $G^6$–$G^9$ are hereinbefore defined;
with $$\underset{O}{\triangle}—G^{15}—SXC$$

wherein $G^{15}$ is as hereinbefore defined.
Preferred ester-alkylene linkages have the formula $$—O—\overset{\overset{O}{\|}}{C}—G^6—\left(\underset{H_2}{C}\right)_2—CH_3$$

wherein $G^7$ is as hereinbefore defined.
These linkages may be prepared by reacting

PSC—OH with $$G^{11}—\overset{\overset{O}{\|}}{C}—G^6—\diagdown$$

and then reacting with a hydrogen-terminated silicone chain compound (i.e. $G^5$=H) over a platinum catalyst.

Emulsions

The silicone and substituted polysaccharide can be provided in the form of an emulsion for use in laundry treatment compositions.

Preferably, an emulsion according to the invention comprises a silicone and a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

The emulsion must contain another liquid component as well as the silicone, preferably a polar solvent, such as water. The emulsion has typically 30 to 99.9%, preferably 40 to 99% of the other liquid component (eg water). Low water emulsions may be for example 30 to 60% water, preferably 40 to 55% water. High water emulsions may be for example 60 to 99.9% water, preferably 80 to 99% water. Moderate water emulsions may be for example 55 to 80% water.

The emulsion may contain an emulsifying agent, preferably an emulsifying surfactant for the silicone and polysaccharide. The emulsifying agent is especially one or more surfactants, for example, selected from any class, sub class or specific surfactant(s) disclosed herein in any context. The emulsifying agent most preferably comprises or consists of a non-ionic surfactant. Additionally or alternatively, one or more selected additional surfactants from anionic, cationic, zwitterionic and amphoteric surfactants may be incorporated in or used as the emulsiflying agent.

Suitable non-ionic surfactants include the (poly) alkoxylated analogues of saturated or unsaturated fatty alcohols, for example, having from 8 to 22, preferably from 9 to 18, more preferably from 10 to 15 carbon atoms on average in the hydrocarbon chain thereof and preferably on average from 3 to 11, more preferably from 4 to 9 alkyleneoxy groups. Most preferably, the alkyleneoxy groups are independently selected from ethyleneoxy, propyleneoxy and butylenoxy, especially ethyleneoxy and propylenoxy, or solely ethyleneoxy groups and alkyl polyglucosides as disclosed in EP 0 495 176.

Preferably, the (poly)alkoxylated analogues of saturated or unsaturated fatty alcohols, have a hydrophilic-lipophilic balance (HLB) of between 8 to 18. The HLB of a polyethoxylated primary alcohol nonionic surfactant can be calculated by $$HLB = \frac{MW(EO)}{MW(TOT) \times 5} \times 100$$

where
MW (EO)=the molecular weight of the hydrophilic part (based on the awerage number of EO groups)
MW(TOT)=the molecular weight of the whole surfactant (based on the average chain length of the hydrocarbon chain)
This is the classical HLB calculation according to Griffin (J. Soc. Cosmentic Chemists, 5 (1954) 249–256).
For analogous nonionics with a mix of ethyleneoxy (EO), propylenoxy (PO) and/or butyleneoxy (BO) hydrophilic groups, the following formula can be used;

$$HLB = \frac{MW(EO) + 0.57\ MW(PO) + 0.4\ MW(BO)}{MW(TOT) \times 5}$$

Preferably, the alkyl polyglucosides may have the following formula;

R—O—$Z_n$ in which R is a linear or branched, saturated or unsaturated aliphatic alkyl radical having 8 to 18 carbon atoms or mixtures thereof, and $Z_n$ is a polyglycosyl radical with n=1.0 to 1.4 hexose or pentose units or mixtures. Preferred examples of alkylpolyglucosides include Glucopon™.

Whether in a composition of a component (especially an emulsion) to be incorporated in a laundry treatment composition as a whole, the weight ratio of silicone to the substituted polysaccharide is preferably from 1:1 to 100:1, more preferably from 5:1 to 20:1. The weight ratio of substituted polysaccharide to emulsifying agent is from 1:2 to 100:1, preferably 2:1 to 10:1. Further, in any such composition (especially emulsion components) the weight ratio of silicone to emulsifying agent is from 100:1 to 2:1, preferably from 100:3 to 5:1, more preferably from 15:1 to 7:1.

Preferably, the total amount of silicone is from 50 to 95%, preferably from 60 to 90%, more preferably from 70 to 85% by weight of the substituted polysaccharide, silicone and any emulsifying agent.

Emulsion Processing

When in the form of an emulsion, the emulsion is prepared by mixing the silicone, substituted polysaccharide, other liquid component (eg water) and preferably, also an emulsifying agent, such as a surfactant, especially a non-ionic surfactant, e.g. in a high shear mixer.

Whether or not pre-emulsified, the silicone and the substituted polysaccharide may be incorporated by admixture with other components of a laundry treatment composition. Preferably, the emulsion is present at a level of from 0.0001 to 40%, more preferably from 0.001 to 30%, even more preferably from 0.1 to 20%, especially from 1 to 15% and for example from 5 to 10% by weight of the total composition.

Laundry Treatment Compositions

The silicone and the substituted polysaccharide are incorporated together into laundry compositions, as separate ingredients or a composition which is an ingredient to be incorporated in the laundry treatment composition, especially as an emulsion. For example, such a composition may optionally also comprise only a diluent (which may comprise solid and/or liquid) and/or also it may comprise an active ingredient. The substituted polysaccharide is typically included in said compositions at levels of from 0.001% to 10% by weight, preferably from 0.005% to 5%, most preferably from 0.01% to 3%.

If an emulsion, typical inclusion levels of the emulsion in the laundry treatment composition are from 0.0001 to 40%, more preferably from 0.001 to 30%, even more preferably from 0.1 to 20%, especially from 1 to 15% and for example from 5 to 10% by weight of the total composition.

The active ingredient in the compositions is preferably a surface active agent or a fabric conditioning agent. More than one active ingredient may be included. For some applications a mixture of active ingredients may be used.

The compositions of the invention may be in any physical form e.g. a solid such as a powder or granules, a tablet, a solid bar, a paste, gel or liquid, especially, an aqueous based liquid. In particular the compositions may be used in laundry compositions, especially in liquid, powder or tablet laundry composition.

The compositions of the present invention are preferably laundry compositions, especially main wash (fabric washing) compositions or rinse-added softening compositions. The main wash compositions may include a fabric softening agent and rinse-added fabric softening compositions may include surface-active compounds, particularly non-ionic surface-active compounds, if appropriate.

The detergent compositions of the invention may contain a surface-active compound (surfactant) which may be chosen from soap and non-soap anionic, cationic, non-ionic, amphoteric and zwitterionic surface-active compounds and mixtures thereof. Many suitable surface-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and non-ionic compounds.

The compositions of the invention may contain linear alkylbenzene sulphonate, particularly linear alkylbenzene sulphonates having an alkyl chain length of $C_8$–$C_{15}$. It is preferred if the level of linear alkylbenzene sulphonate is from 0 wt % to 30 wt %, more preferably 1 wt % to 25 wt %, most preferably from 2 wt % to 15 wt %.

The compositions of the invention may contain other anionic surfactants in amounts additional to the percentages quoted above. Suitable anionic surfactants are well-known to those skilled in the art. Examples include primary and secondary alkyl sulphates, particularly $C_8$–$C_{15}$ primary alkyl sulphates; alkyl ether sulphates; olefin sulphonates; alkyl xylene sulphonates; dialkyl sulphosuccinates; and fatty acid ester sulphonates. Sodium salts are generally preferred.

The compositions of the invention may also contain non-ionic surfactant. Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %.

Any conventional fabric conditioning agent may be used in the compositions of the present invention. The conditioning agents may be cationic or non-ionic. If the fabric conditioning compound is to be employed in a main wash detergent composition the compound will typically be non-ionic. For use in the rinse phase, typically they will be cationic. They may for example be used in amounts from 0.5% to 35%, preferably from 1% to 30% more preferably from 3% to 25% by weight of the composition.

Suitable cationic fabric softening compounds are substantially water-insoluble quaternary ammonium materials comprising a single alkyl or alkenyl long chain having an average chain length greater than or equal to $C_{20}$ or, more preferably, compounds comprising a polar head group and two alkyl or alkenyl chains having an average chain length greater than or equal to $C_{14}$. Preferably the fabric softening compounds have two long chain alkyl or alkenyl chains each having an average chain length greater than or equal to $C_{16}$. Most preferably at least 50% of the long chain alkyl or alkenyl groups have a chain length of $C_{18}$ or above. It is preferred if the long chain alkyl or alkenyl groups of the fabric softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surfactants Science Series" volume 34 ed. Richmond 1990, volume 37 ed. Rubingh 1991 and volume 53 eds. Cross and Singer 1994, Marcel Dekker Inc. New York".

Any of the conventional types of such compounds may be used in the compositions of the present invention.

The fabric softening compounds are preferably compounds that provide excellent softening, and are characterised by a chain melting $L_\beta$ to $L_{60}$ transition temperature greater than 25° C., preferably greater than 35° C., most preferably greater than 45° C. This $L_\beta$ to $L_\alpha$ transition can be measured by differential scanning calorimetry as defined in "Handbook of Lipid Bilayers", D Marsh, CRC Press, Boca Raton, Fla., 1990 (pages 137 and 337).

Substantially water-insoluble fabric softening compounds are defined as fabric softening compounds having a solubility of less than $1\times10^{-3}$ wt % in demineralised water at 20° C. Preferably the fabric softening compounds have a solubility of less than $1\times10^{-4}$ wt %, more preferably less than $1\times10^{-8}$ to $1\times10^{-6}$ wt %.

Especially preferred are cationic fabric softening compounds that are water-insoluble quaternary ammonium materials having two $C_{12-22}$ alkyl or alkenyl groups connected to the molecule via at least one ester link, preferably two ester links. An especially preferred ester-linked quaternary ammonium material can be represented by the formula:

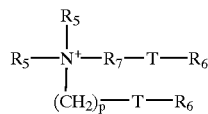

wherein each $R_5$ group is independently selected from $C_{1-4}$ alkyl or hydroxyalkyl groups or $C_{2-4}$ alkenyl groups; each $R_6$ group is independently selected from $C_{8-28}$ alkyl or alkenyl groups; and wherein $R_7$ is a linear or branched alkylene group of 1 to 5 carbon atoms, T is

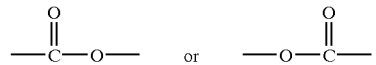

and p is 0 or is an integer from 1 to 5.

Di(tallowoxyloxyethyl) dimethyl ammonium chloride and/or its hardened tallow analogue is an especially preferred compound of this formula.

A second preferred type of quaternary ammonium material can be represented by the formula:

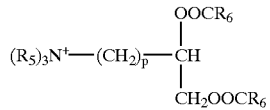

wherein $R_5$, p and $R_6$ are as defined above.

A third preferred type of quaternary ammonium material are those derived from triethanolamine (hereinafter referred to as 'TEA quats') as described in for example U.S. Pat. No. 3,915,867 and represented by formula:

wherein T is H or ($R_8$—CO—) where $R_8$ group is independently selected from $C_{8-28}$ alkyl or alkenyl groups and $R_g$ is $C_{1-4}$ alkyl or hydroxyalkyl groups or $C_{2-4}$ alkenyl groups. For example N-methyl-N,N,N-triethanolamine ditallowester or di-hardened-tallowester quaternary ammonium chloride or methosulphate. Examples of commercially available TEA quats include Rewoquat WE18 and Rewoquat WE20, both partially unsaturated (ex. WITCO), Tetranyl AOT-1, fully saturated (ex. KAO) and Stepantex VP 85, fully saturated (ex. Stepan).

It is advantageous if the quaternary ammonium material is biologically biodegradable.

Preferred materials of this class such as 1,2-bis(hardened tallowoyloxy)-3-trimethylammonium propane chloride and their methods of preparation are, for example, described in U.S. Pat. No. 4,137,180 (Lever Brothers Co). Preferably these materials comprise small amounts of the corresponding monoester as described in U.S. Pat. No. 4,137,180, for example, 1-hardened tallowoyloxy-2-hydroxy-3-trimethylammonium propane chloride.

Other useful cationic softening agents are alkyl pyridinium salts and substituted imidazoline species. Also useful are primary, secondary and tertiary amines and the condensation products of fatty acids with alkylpolyamines.

The compositions may alternatively or additionally contain water-soluble cationic fabric softeners, as described in GB 2 039 556B (Unilever).

The compositions may comprise a cationic fabric softening compound and an oil, for example as disclosed in EP-A-0829531.

The compositions may alternatively or additionally contain nonionic fabric softening agents such as lanolin and derivatives thereof.

Lecithins and other phospholipids are also suitable softening compounds.

In fabric softening compositions nonionic stabilising agent may be present. Suitable nonionic stabilising agents may be present such as linear $C_8$ to $C_{22}$ alcohols alkoxylated with 10 to 20 moles of alkylene oxide, $C_{10}$ to $C_{20}$ alcohols, or mixtures thereof. Other stabilising agents include the deflocculating polymers as described in EP 0415698A2 and EP 0458599 B1.

Advantageously the nonionic stabilising agent is a linear $C_8$ to $C_{22}$ alcohol alkoxylated with 10 to 20 moles of alkylene oxide. Preferably, the level of nonionic stabiliser is within the range from 0.1 to 10% by weight, more preferably from 0.5 to 5% by weight, most preferably from 1 to 4% by weight. The mole ratio of the quaternary ammonium compound and/or other cationic softening agent to the nonionic stabilising agent is suitably within the range from 40:1 to about 1:1, preferably within the range from 18:1 to about 3:1.

The composition can also contain fatty acids, for example $C_8$ to $C_{24}$ alkyl or alkenyl monocarboxylic acids or polymers thereof. Preferably saturated fatty acids are used, in particular, hardened tallow $C_{16}$ to $C_{18}$ fatty acids. Preferably the fatty acid is non-saponified, more preferably the fatty acid is free, for example oleic acid, lauric acid or tallow fatty acid. The level of fatty acid material is preferably more than 0.1% by weight, more preferably more than 0.2% by weight. Concentrated compositions may comprise from 0.5 to 20% by weight of fatty acid, more preferably 1% to 10% by weight. The weight ratio of quaternary ammonium material or other cationic softening agent to fatty acid material is preferably from 10:1 to 1:10.

It is also possible to include certain mono-alkyl cationic surfactants which can be used in main-wash compositions for fabrics. Cationic surfactants that may be used include quaternary ammonium salts of the general formula $R_1R_2R_3R_4N^+X^-$ wherein the R groups are long or short hydrocarbon chains, typically alkyl, hydroxyalkyl or ethoxylated alkyl groups, and X is a counter-ion (for example, compounds in which $R_1$ is a $C_8$–$C_{22}$ alkyl group, preferably a $C_8$–$C_{10}$ or $C_{12}$–$C_{14}$ alkyl group, $R_2$ is a methyl group, and $R_3$ and $R_4$, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The total amount of surfactant present will also depend on the intended end use and may be as high as 60 wt %, for example, in a composition for washing fabrics by hand. In compositions for machine washing of fabrics, an amount of from 5 to 40 wt % is generally appropriate. Typically the compositions will comprise at least 2 wt % surfactant e.g. 2–60%, preferably 15–40% most preferably 25–35%.

Detergent compositions suitable for use in most automatic fabric washing machines generally contain anionic non-soap surfactant, or non-ionic surfactant, or combinations of the two in any suitable ratio, optionally together with soap.

The compositions of the invention, when used as main wash fabric washing compositions, will generally also contain one or more detergency builders. The total amount of detergency builder in the compositions will typically range from 5 to 80 wt %, preferably from 10 to 60 wt %.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50 wt %.

The alkali metal aluminosilicate may be either crystalline or amorphous or mixtures thereof, having the general formula: $0.8–1.5\ Na_2O.\ Al_2O_3.\ 0.8–6\ SiO_2$ These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature. Suitable crystalline sodium aluminosilicate ion-exchange detergency builders are described, for example, in GB 1 429 143 (Procter & Gamble). The preferred sodium aluminosilicates of this type are the well-known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium weight ratio not exceeding 1.33, preferably within the range of from 0.90 to 1.33, and more preferably within the range of from 0.90 to 1.20.

Especially preferred is zeolite MAP having a silicon to aluminium weight ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di and trisuccinates, carboxymethyloxy succinates, carboxymethyloxymalonates, dipicolinates, hydroxyethyliminodiacetates, alkyl- and alkenylmalonates and succinates; and sulphonated fatty acid salts. This list is not intended to be exhaustive.

Especially preferred organic builders are citrates, suitably used in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N', N',-tetracetyl ethylenediamine (TAED) and sodium nonanoyloxybenzene sulphonate (SNOBS). The novel quaternary ammonium and phosphonium bleach precursors disclosed in U.S. Pat. Nos. 4,751,015 and 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. examples of such peracids can be found in U.S. Pat. Nos. 4,686,063 and 5,397,501 (Unilever). A preferred example is the imido peroxycarboxylic class of peracids described in EP A 325 288, EP A 349 940, DE 382 3172 and EP 325 289. A particularly preferred example is phthalimido peroxy caproic acid (PAP). Such peracids are suitably present at 0.1–12%, preferably 0.5–10%.

A bleach stabiliser (transition metal sequestrant) may also be present. Suitable bleach stabilisers include ethylenediamine tetra-acetate (EDTA), the polyphosphonates such as Dequest (Trade Mark) and non-phosphate stabilisers such as EDDS (ethylene diamine di-succinic acid). These bleach stabilisers are also useful for stain removal especially in products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

The compositions according to the invention may also contain one or more enzyme(s). Suitable enzymes include the proteases, amylases, cellulases, oxidases, peroxidases and lipases usable for incorporation in detergent compositions. Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4–12 are available and can be used in the instant invention. Examples of suitable proteolytic enzymes are the subtilisins which are obtained from particular strains of *B. Subtilis B. licheniformis*, such as the commercially available subtilisins Maxatase (Trade Mark), as supplied by Genencor International N.V., Delft, Holland, and Alcalase (Trade Mark), as supplied by Novozymes Industri A/S, Copenhagen, Denmark.

Particularly suitable is a protease obtained from a strain of Bacillus having maximum activity throughout the pH range of 8–12, being commercially available, e.g. from Novozymes Industri A/S under the registered trade-names Esperase (Trade Mark) and Savinase (Trade-Mark). The preparation of these and analogous enzymes is described in GB 1 243 785. Other commercial proteases are Kazusase (Trade Mark obtainable from Showa-Denko of Japan), Optimase (Trade Mark from Miles Kali-Chemie, Hannover, West Germany), and Superase (Trade Mark obtainable from Pfizer of U.S.A.).

Detergency enzymes are commonly employed in granular form in amounts of from about 0.1 to about 3.0 wt %. However, any suitable physical form of enzyme may be used.

The compositions of the invention may contain alkali metal, preferably sodium carbonate, in order to increase detergency and ease processing. Sodium carbonate may suitably be present in amounts ranging from 1 to 60 wt %, preferably from 2 to 40 wt %. However, compositions containing little or no sodium carbonate are also within the scope of the invention.

Powder flow may be improved by the incorporation of a small amount of a powder structurant, for example, a fatty acid (or fatty acid soap), a sugar, an acrylate or acrylate/maleate copolymer, or sodium silicate. One preferred powder structurant is fatty acid soap, suitably present in an amount of from 1 to 5 wt %.

Other materials that may be present in detergent compositions of the invention include sodium silicate; antiredeposition agents such as cellulosic polymers; soil release polymers; inorganic salts such as sodium sulphate; or lather boosters as appropriate; proteolytic and lipolytic enzymes; dyes; coloured speckles; fluorescers and decoupling polymers. This list is not intended to be exhaustive. However, many of these ingredients will be better delivered as benefit agent groups in materials according to the first aspect of the invention.

The detergent composition when diluted in the wash liquor (during a typical wash cycle) will typically give a pH of the wash liquor from 7 to 10.5 for a main wash detergent.

Particulate detergent compositions are suitably prepared by spray-drying a slurry of compatible heat-insensitive ingredients, and then spraying on or post-dosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l. Especially preferred compositions have bulk densities of at least 650 g/litre, more preferably at least 700 g/litre.

Such powders may be prepared either by post-tower densification of spray-dried powder, or by wholly non-tower methods such as dry mixing and granulation; in both cases a high-speed mixer/granulator may advantageously be used. Processes using high-speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

Product Forms

Product forms include powders, liquids, gels, tablets, any of which are optionally incorporated in a water-soluble or water dispersible sachet. The means for manufacturing any of the product forms are well known in the art. If the silicone and the substituted polysaccharide are to be incorporated in a powder (optionally the powder to be tableted), and whether or not pre-emulsified, they are optionally included in a separate granular component, e.g. also containing a water soluble organic or inorganic material, or in encapsulated form.

Substrate

The substrate may be any substrate onto which it is desirable to deposit silicones and which is subjected to treatment such as a washing or rinsing process.

In particular, the substrate may be a textile fabric. It has been found that particular good results are achieved when using a natural fabric substrate such as cotton, or fabric blends containing cotton.

Treatment

The treatment of the substrate with the material of the invention can be made by any suitable method such as washing, soaking or rinsing of the substrate.

Typically the treatment will involve a washing or rinsing method such as treatment in the main wash or rinse cycle of a washing machine and involves contacting the substrate with an aqueous medium comprising the material of the invention.

The present invention will now be explained in more detail by reference to the following non-limiting examples:

In the following examples where percentages are mentioned, this is to be understood as percentage by weight. In the following tables where the values do not add up to 100 these are to be understood as parts by weight.

EXAMPLE A

Sample Synthesis of an Ester Linked Cellulose Monoacetate (CMA) with Grafted Silicone Monocarboxydecyl terminated polydimethylsiloxane (PDMS) source (Mwt 5,000: 1.5 g, 0.23 mmols) was dispersed in dimethylacetamide (10 cm$^3$) by vigorous stirring under nitrogen. Carbonyldiimidazole (37 mg, 0.23 mmols)

was then added and the dispersion heated with stirring to 70° C. under nitrogen for two hours. A solution of cellulose monoacetate (DS 0.58; 1 g, 5.3 mmol equivalents based on primary hydroxyl groups) in dimethylacetamide (10 cm$^3$) was then added and stirring and heating was continued for a further 20 hours. Following this time the mixture was filtered and the filtrate added to vigorously stirring acetone to give a white precipitate. This precipitate was filtered off, washed with acetone and dried under vacuum to give a white polymer (1.01 g). From the $^1$H NMR of the polymer (after hydrolysis of 20% DCl in D$_2$O for two hours at 80° C.) and normalising the integration of the anomeric protons to unity and the acetate group to 0.58 the Si—CH$_3$ group (at 0.0 ppm) integration gives an overall degree of substitution (DS) of siloxane groups of 0.0015 (hereinafter referred to as "Polymer A").

Example 1

Model washes were done in 200 ml, pots were prepared and treated as follows:

| Per pot | 0.1 liter of wash liquor |
| | enough composition to give 3.0 mg silicone per gram of cotton |
| | 1 piece of mercerised cotton 20 × 20 cm |
| | wash at 40° C. for 30 mins, bottleshaker at shake speed of ~100 shakes per minute |
| | rinse, 2 × 200 ml tap water (nominal hardness 24° FH). |
| | Fabric dried o/n on a flat surface of ambient temperature |

The wash liquor for example 1 and the control were as follows:

| Ingredient | Example 1 | Quantity g/L in H$_2$O Control |
|---|---|---|
| Wash Liquor | | |
| NaCl | 0.6 | 0.6 |
| Sodium Tripolyphosphate | 0.66 | 0.66 |
| Na$_2$CO$_3$ | 0.75 | 0.75 |
| Na alkyl benzene sulphonate | 0.6 | 0.6 |
| Nonionic* | 0.19 | 0.19 |
| Pre formed Emulsion (2% in H$_2$O) | | |
| Tween 20 | 0.009 | 0.009 |
| PDMS | 0.18 | 0.18 |
| Polymer A | 0.018 (post dosed) | — |

*Average C$_{10}$ fatty alcohol ethyoxylated with an average of 6 ethylene oxide units.

Fabrics were then analysed for silicone depositing according to the following protocol:

Solvent extraction of silicones from fabric. Use 10 ml THF/g of cotton
extract at room temperature for 24 hrs with constant agitation.
analyse THF for silicone levels via gel permeation chromatography (GPC), using evaporative light scattering detector.

The deposition analysis gave the following results
Results Target dose=3 mg/g

| | mg/g | % deposit |
|---|---|---|
| Control | 0.5 | 16.6 |
| Example 1 | 1.5 | 50 |

Example 2

This example shows that the deposition is even further enhanced if the emulsion is prepared with a co-surfactant and Polymer A introduced at the beginning of the emulsification step.

Model washes were done in 200 ml, pots were prepared and treated as follows:

| Per pot | 0.1 liter of wash liquor |
| | enough composition to give 2.0 mg silicone per gram of cotton |
| | 2 piece of mercerised cotton 20 × 20 cm |
| | wash at 40° C. for 30 mins, bottleshaker at shake speed of ~100 shakes per minute |
| | rinse, 2 × 200 ml tap water (nominal hardness 24° FH). |
| | fabric dried o/n on a flat surface of ambient temperature |

The wash liquor for example 2 and the control were as follows:

| Ingredient | Example 2 | Quantity g/L in H$_2$O Control |
|---|---|---|
| Wash Liquor | As in Example 1 | As in Example 1 |
| Pre formed Emulsion (2% in H$_2$O) | | |
| Amino Silicone (Q2-2880) | 0.24 | 0.24 |
| Polymer A | 0.024 | — |
| A7 | 0.0072 | 0.0072 |

Analysed as per Example 1.
Results Target dose=2 mg/g

| | mg/g | % deposit |
|---|---|---|
| Control | 0.07 | 3.4 |
| Example 2 | 1.66 | 83 |

Example 3

This example shows that deposition is even further enhanced if the product is delivered by means of a detergent powder.

Model washes were done in 200 ml, pots were prepared and treated as follows:

| Per pot | 0.1 liter of wash liquor |
| | enough composition to give 16.7 mg silicone per gram of cotton |
| | 1 piece of mercerised cotton 20 × 20 cm |
| | wash at 40° C. for 30 mins, bottleshaker at shake speed of ~100 |

-continued shakes per minute
rinse, 2 × 200 ml tap water (nominal hardness 24° FH).
fabric dried o/n on a flat surface of ambient temperature The wash liquor for example 3 and the control were as follows:

Emulsions were prepared as follows:

| Ingredient | Example 3 | Quantity g/L in H₂O Control |
|---|---|---|
| Pre formed Emulsion | | |
| (2% in H₂O) | | |
| Amino Silicone (Q2-2880) | 1 | 1 |
| Polymer A | 0.1 | — |
| A7 | 0.03 | 0.03 |

Example 3 and the control were evaluated as per Example 1 with the exception that a detergent powder of the following composition was used.

| TYPE | INGREDIENTS | wt % |
|---|---|---|
| ACTIVES | Anionic (LAS) | 23.00 |
| | Nonionic 7EO | |
| | Cationic (Praepagen HY) | 0.80 |
| BUILDERS | STPP | 14.50 |
| METAL CHELATING AGENT | DEQUEST 2047 | |
| POLYMERS | Narlex LD30 | |
| SOIL RELEASE POLYMER | Gerol | |
| ANTIREDEP | SCMC | 0.37 |
| ANTI-FOAM | Silicone incorrporating granule | |
| MINORS | | 0.24 |
| FLUORESCER | | 0.07 |
| | | 0.12 |
| BLEACH | Perborate Tetrahydrated | |
| | Perborate monohydrated | |
| | TEAD | |
| ENZYME | Lipolase 100T | 0.19 |
| | Amylase 60T | 0.28 |
| | Savinase 12T | 0.47 |
| COLORANT | C174160 | 0.02 |
| | Blue dispersor | |
| INORGANIC SALTS | Citric Acid | |
| | Speckles (STPP) | |
| | Sodium Carbonate | 17.50 |
| | Sodium Bicarbonate | |
| | Sodium Sulphate | 28.52 |
| | Sodium Clorite | |
| | Sodium Silicate | 7.00 |

The resultant mixture was dosed at 5.1 g/l in water in the apparatus of Example 1.

Further, 0.3 g of spray dried emulsion of Example 3 was post-dosed to 0.21 g a detergent powder of the following composition:

In the following results of the evaluated deposition of silicone, "Example 3A" refers to the detergent powder/spray dried emulsion referred to above.

Results Target dose 16.6 mg/g silicone per gram of cotton

| | mg/g | % |
|---|---|---|
| Control | 0.65 | 3.5 |
| Example 3 | 6.36 | 38.3 |
| Example 3A | 10.46 | 63 |

Formulation Examples 4–8

Raw material specification:

| Component | Specification |
|---|---|
| LAS | Alkyl Benzene Sulphonic-acid, Marion AS3, ex Huls |
| LES | Linear ether sulfate |
| A7 | Synperonic A7 (C13–15 EO7) |
| TAED | Tetraacetate ethylene diamine |
| Tween 20 | Polyoxyethylenesorbitan (POE) 20 sorbitan monolaurate (Polyethylene glycol sorbitan monolaurate) |
| EDTMP | Ethylene diaminetetramethylene phosphonate |
| CMC | Carboxymethyl cellulose |
| Nabion 15 | Carbonate/disilicate co-granule |
| PVP | Dye transfer inhibitor |
| EDHP | Sequestering agent |
| Na-PAS | Primary Alkyl Benzene Sulphonic-acid, neutralised with NaOH |
| Dobanol 25-7 | $C_{12-15}$ ethoxylated alcohol, 7EO, ex shell |
| Zeolite | Wassalith P, ex Degussa |
| STPP | Sodium Tri Polyphosphate, Thermphos NW, ex Hoechst |
| Dequest 2066 | Metal chelating agent, ex Monsanto |
| Lipolase | Type 100L, ex Novo |
| Savinase 16L | Protease, ex Novo |
| Sokalan CP5 | Acrylic/Maleic Builder Polymer, ex BASF |
| Defloculating Polymer | Polymer A-11 disclosed in EP-A-346 995 |
| SCMC | Sodium Carboxymethyl Cellulose |
| Minors | Antiredeposition polymers, transition-metal scavangers/bleach stabilisers, fluorescers, dye-transfer-inhibition polymers, enzymes |
| Polymer A | Material Specified in Example A. |

Example 4

Tablet Formulation

| | Phosphate (%) | Acetate (%) |
|---|---|---|
| Anionic Surfactant (LAS) | 7.5 | 8.5 |
| Nonionic Surfactant (7EO) | 3.5 | 4 |
| Soap | 0.6 | 0.6 |
| Zeolite MAP | 15.5 | 19 |
| Na-acetate | 2.5 | 25 |
| Sodium tripolyphosphate (High Phase A) | 32 | |
| Na-disilicate | 2.5 | 2.5 |
| Phosphonates | 0.6 | 1 |
| Sodium carbonate | 2.8 | 3 |
| TAED | 3 | 4 |
| Sodium percarbonate | 11 | 14 |
| Enzymes | 1 | 1 |
| Minors (eg Fluorescer, Antifoam adjuncts, moisture) | 6.5 | 6.5 |
| Granule* | 11 | 11 |
| | 100 | 100.1 |

*A granule of emulsion of CMA-grafted silicone (Polymer A), silicone and nonionic surfactant (2% total in H₂O) granulated with carrier.

Example 5

Standard Powder Formulation

| Ingredient | Level (%) |
| --- | --- |
| Na-LAS | 8.75 |
| NI 7EO | 6.83 |
| Soap | 1.44 |
| Zeolite | 19.78 |
| Copolymer CP5 | 0.76 |
| Na silicate | 0.73 |
| Na carbonate | 11.81 |
| Na sulfate | 7.06 |
| CMC | 0.29 |
| Moisture & Salts | 5.0 |
| TAED 83% | 2.50 |
| Na percarbonate | 12.25 |
| Fluoresecer | 0.8 |
| EDTMP | 0.65 |
| EHDP | 0.45 |
| Carbonate/Disilicate | 3.35 |
| Citric acid | 2.55 |
| Enzyme | 0.5 |
| Minors | 2.50 |
| Granule as example 4 | 12.00 |

Example 6

Concentrate Powder Formulation

| Ingredient | Level (%) |
| --- | --- |
| LAS acid | 8.30 |
| Sodium hydroxide | 0.50 |
| NI 7EO | 7.0 |
| Zeolite | 19.90 |
| Na carbonate | 8.90 |
| CMC | 0.35 |
| Moisture & Salts | 4.0 |
| TAED 83% | 5.0 |
| Na percarbonate | 20.00 |
| Fluorescer | 1.30 |
| Nabion 15 | 5.50 |
| EDTMP | 0.90 |
| EHDP | 0.50 |
| Carbonate | 2.50 |
| Sodium citrate | 2.00 |
| Enzyme | 0.90 |
| Minors | 0.45 |
| Granule as example 4 | 12.0 |

Example 7

Concentrate Liquid Formuation

| Ingredient | Level (%) | Level (%) |
| --- | --- | --- |
| Nonionic 7 EO | 21.00 | 8.00 |
| LES |  | 8.00 |
| LAS |  | 8.00 |
| Fatty acid | 12.87 | 8.00 |
| Citric Acid | 1.00 |  |
| Antiredeposition polymer | 0.41 | 0.41 |
| Sodium Hydroxide - 50% |  | 3.10 |
| Potassium hydroxide | 3.88 |  |
| Preservative | 0.01 | 0.01 |
| Propylene Glycol | 9.00 | 4.00 |
| NaCl |  | 1.00 |
| Boric Acid | 1.00 | 1.00 |
| Fluoroscer | 0.05 | 0.05 |
| Base liquid | 49.22 | 41.57 |
| Water & salts | 37.44 | 45.09 |
|  | 86.66 | 86.66 |
| PVP (30%) | 0.30 | 0.30 |
| Silicone antifoam |  |  |
| Enzyme | 0.50 | 0.50 |
| EHDP | 1.00 | 1.00 |
| Minors (average) | 0.54 | 0.54 |
| Granule as example 4 | 11.00 | 11.00 |
| Total | 100.0 | 100.0 |

Example 8

Dilute Liquid Formulation

| Ingredient | Example A Inclusion level (%) | Example B Inclusion level (%) |
| --- | --- | --- |
| Nonionic 7 EO | 11.36 | 4.50 |
| LES |  | 4.50 |
| LAS |  | 4.50 |
| Fatty acid | 6.69 | 4.50 |
| Citric Acid | 1.50 |  |
| Antiredeposition polymer | 0.23 | 0.25 |
| Sodium Hydroxide - 50% |  | 1.91 |
| Potassium hydroxide | 3.06 |  |
| Preservative | 0.02 | 0.02 |
| Propylene Glycol | 6.00 | 4.00 |
| NaCl |  | 1.50 |
| Boric Acid | 1.00 | 1.00 |
| Fluorescer | 0.02 | 0.02 |
| base liquid | 29.88 | 26.70 |
| Water & salts | 57.87 | 61.05 |
|  | 87.75 | 87.75 |
| PVP (30%) | 0.05 | 0.05 |
| Silicone antifoam |  |  |
| Enzyme | 0.30 | 0.30 |
| EHDP | 0.50 | 0.50 |
| Minors | 0.40 | 0.40 |
| Granule as example 4 | 11.00 | 11.00 |
| Total | 100.00 | 100.00 |

Example 9

Soluble Sachet Formulation

A soluble sachet containing the following detergent powder was prepared. The sachet was made in the form of a rectangular package of water-soluble film produced by thermoforming a recess followed by filling and water-sealing the top with a second film. A first sheet of polyvinyl alcohol film (85 micrometer thickness) was used to form the recess.

A detergent powder was made of the following composition by pregranulating the base powder ingredients, followed by post-dosing the rest of the ingredients

| Ingredient | Level (%) |
| --- | --- |
| Na-LAS | 8.75 |
| NI 7EO | 6.83 |
| Soap | 1.44 |
| Zeolite | 19.78 |
| Copolymer CP5 | 0.76 |
| Na silicate | 0.73 |
| Na carbonate | 11.81 |
| Na sulfate | 7.06 |
| CMC | 0.29 |
| Moisture & Salts | 5.0 |
| TAED 83% | 2.50 |
| Na percarbonate | 12.25 |
| Fluoresecer | 0.8 |
| EDTMP | 0.65 |
| EHDP | 0.45 |
| Carbonate/Disilicate | 3.35 |
| Citric acid | 2.55 |
| Enzyme | 0.5 |
| Minors | 2.50 |
| Granule as example 4 | 12.0 |

This detergent powder was dosed in the recess of the soluble sachet. After the powder was added, a second sheet of polyvinylalcohol (45 micron thickness) was added on top of the compartment and sealed to the first sheet along a continuous region to form a closed water soluble sachet containing the detergent powder.

Example 10

Soluble Sachet Formulation

| Raw Material | % |
| --- | --- |
| Nonionic | 24.00 |
| Pigment Premix/dye | 0.020 |
| Monopropylene glycol | 4.95 |
| Glycerol | 19.5 |
| Monoethanolamine | 6.9 |
| Fatty Acid (oleic) | 11.90 |
| Softened water | 2.28 |
| LAS Acid | 18.10 |
| Minors | 1.45 |
| Enzymes | 0.9 |
| Granule as example 4 | 10.00 |
| Total | 100 |

The sachet was prepared in accordance with the method of Example 9.

What is claimed is:

1. A composition comprising an emulsifying agent, a silicone and a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, wherein the silicone and the substituted polysaccharide are in the form of an emulsion, the substituted polysaccharide further comprising one or more independently selected silicone chains; and wherein the total amount of silicne is from 50 to 95% by weight of the substituted polysaccharide, silicone and any emulsifying agent.

2. The emulsion of claim 1 wherein the emulsifying agent comprises a non-ionic surfactant.

3. The emulsion of claim 1 wherein the emulsion is 30 to 99.9% of another liquid component.

4. The composition of claim 1 wherein the weight ratio of silicone to emulsifying agent is from 100:1 to 2:1.

5. The composition of claim 1 wherein the weight ratio of silicone to the substituted polysaccharide is from 1:1 to 100:1.

6. The composition of claim 1 wherein the substituted polysaccharide comprises only $\beta_{1-4}$ linkages.

7. The composition of claim 1 wherein the substituted polysaccharide comprises additional linkages.

8. The composition of claim 7 wherein the substituted polysaccharide comprises $\beta_{1-4}$ and $\beta_{1-3}$ linkages.

9. The composition of claim 8 wherein the weight ratio of $\beta_{1-3}$ to $\beta_{1-4}$ linkages is from 1:100 to 1:2.

10. The composition of claim 1 wherein the silicone is selected from polydialkyl siloxanes, amine derivatives thereof, and mixtures thereof.

11. The composition of claim 1, wherein the average degree of substitution of the silicone chain(s) on the substituted polysaccharide is from 0.001 to 0.5.

12. The composition of claim 1, wherein the silicone chain(s) in the substituted polysaccharide is or are independently selected from those of formula:

$$-L-\underset{\underset{G^3}{|}}{\overset{\overset{G^1}{|}}{Si}}-G^2$$

wherein L is absent or is a linking group and one or two of substituents $G^1$–$G^3$ is a methyl group, the remainder being selected from groups of formula $$-O-\left(\underset{\underset{CH_3}{|}}{\overset{\overset{CH_3}{|}}{Si}}-O\right)_n-\left(\underset{\underset{G^4}{|}}{\overset{\overset{CH_3}{|}}{Si}}-O\right)_m-\underset{\underset{CH_3}{|}}{\overset{\overset{CH_3}{|}}{Si}}-G^5$$

the —Si(CH$_3$)$_2$O— groups and the —Si(CH$_3$O)(G$^4$)— groups being arranged in random or block fashion;

wherein n is from 5 to 1000, and m is from 0 to 100;

G$^4$ is selected from groups of formula:

—(CH$_2$)$_p$—CH$_3$, where p is from 1 to 18

—(CH$_2$)$_q$—NH—(CH$_2$)$_r$, —NH$_2$ where q and r are independently from 1 to 3

—(CH$_2$)$_s$—NH$_2$, where s is from 1 to 3

$$\underset{CH-CH_2}{\overset{O}{\triangle}}$$

—(CH$_2$)$_t$— where t is from 1 to 3

—(CH$_2$)$_u$—COOH, where u is from 1 to 10,

[lactone/succinic anhydride group with —(CH$_2$)$_v$—]

where v is from 1 to 10, and

—(CH$_2$ CH$_2$O)$_w$—(CH$_2$)$_x$ H, where w is from 1 to 150, and x is from 0 to 10;

and G⁵ is independently selected from hydrogen, groups defined above for G⁴, —OH, —CH₃ and —C(CH₃)₃.

13. The composition of claim 12, where L is selected from amide linkages, ester linkages, ether linkages, urethane linkages, triazine linkages, carbonate linkages, amine linkages and ester-alkylene linkages.

14. The composition of claim 1, wherein the chemical change of the relevant group in the substituted polysaccharide is hydrolysis, perhydrolysis or bond-cleavage.

15. The composition of claim 1, wherein the group(s) in the substituted polysaccharide which undergo the chemical change comprise one or more groups attached via an ester linkage to the polysaccharide.

16. The composition of claim 1, wherein the substituted polysaccharide has the general formula (I):

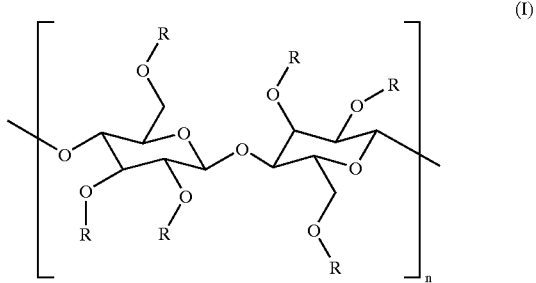
(I)

wherein at least one or more —OR groups of the polymer are independently substituted or replaced by silicone chains and at least one or more R groups are independently selected from groups of formulae:

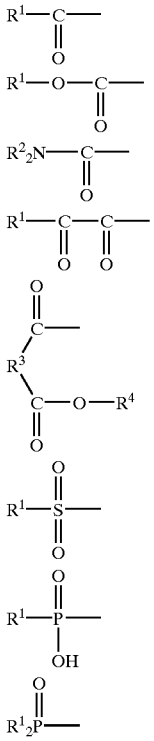

wherein each $R^1$ is independently selected from $C_{1-20}$ alkyl, $C_{2-20}$ alkenyl and $C_{5-7}$ aryl any of which is optionally substituted by one or more substituents independently selected from $C_{1-4}$ alkyl, $C_{1-12}$ alkoxy, hydroxyl, vinyl and phenyl groups;

each $R^2$ is independently selected from hydrogen and groups $R^1$ as hereinbefore defined;

$R^3$ is a bond or is selected from $C_{1-4}$ alkylene, $C_{2-4}$ alkenylene and $C_{5-7}$ arylene groups, the carbon atoms in any of these being optionally substituted by one or more substituents independently selected from $C_{1-12}$ alkoxy, vinyl, hydroxyl, halo and amine groups;

each $R^4$ is independently selected from hydrogen, counter cations such as alkali metal or ½ Ca or ½ Mg, and groups $R^1$ as hereinbefore defined; and groups R which together with the oxygen atom forming the linkage to the respective saccharide ring forms an ester or hemi-ester group of a tricarboxylic- or higher polycarboxylic- or other complex acid such as citric acid, an amino acid, a synthetic amino acid analogue or a protein;

any remaining R groups being selected from hydrogen and other substituents.

17. The composition of claim 15, wherein the ester-linked group(s) is/are selected from carboxylic acid esters.

18. The composition of claims 15, wherein the ester-linked group(s) is/are independently selected from one or more of acetate, propanoate, trifluroacetate, 2-(2-hydroxy-1-oxopropoxy) propanoate, lactate, glycolate, pyruvate, crotonate, isovalerate, cinnamate, formate, salicylate, carbamate, methylcarbamate, benzoate, gluconate, methanesulphonate, toluene sulphonate, groups and hemiester groups of fumaric, malonic, itaconic, oxalic, maleic, succinic, tartaric, aspartic, glutamic, and malic acids.

19. The composition of claim 1, wherein the average degree of substitution on the saccharide rings of the substituted polysaccharide, of the groups which undergo the chemical change is from 0.1 to 3.

20. The composition of claim 1, wherein the substituted polysaccharide further comprises one or more other pendant groups which are neither silicone chains nor groups which undergo a chemical change to enhance substrate affinity.

21. The composition of claim 20, wherein the average degree of substitution of other pendant groups is from 0.001 to 0.5.

22. The composition of claim 1, wherein the total amount of the substituted polysaccharide is from 0.001% to 10% by weight of the total composition.

23. The composition of claim 1 wherein at least the silicone and the substituted polysaccharide emulsion is present in an amount of from 0.0001 to 40% by weight of the total composition.

24. The composition of claim 1, wherein the total amount of silicone is from 0.0001% to 25% by weight of the total composition.

25. A method of depositing a silicone onto a substrate, the method comprising contacting in an aqueous solution, the substrate and a composition comprising a silicone and a substituted polysaccharide in the form of an emulsion, the polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains; and wherein the total amount of silicone is from 50 to 95% by weight of the substituted polysaccharide, silicone and any emulsifying agent.

26. A method of enhancing the softening benefit of a laundry treatment composition on a substrate, the method comprising applying a composition comprising a silicone and a substituted polysaccharide in the form of an emulsion, the polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains; and wherein the total amount of silicone is from 50 to 95% by weight of the substituted polysaccharide, silicone and any emulsifying agent to a substrate.

* * * * *